(12) United States Patent
Grosse

(10) Patent No.: US 7,987,861 B2
(45) Date of Patent: Aug. 2, 2011

(54) HYGIENIC DENTAL FLOSS

(76) Inventor: Ted K. Grosse, Hendersonville, NC (US)

( * ) Notice: Subject to any disclaimer, the term of this patent is extended or adjusted under 35 U.S.C. 154(b) by 651 days.

(21) Appl. No.: 12/009,507

(22) Filed: Jan. 18, 2008

(65) Prior Publication Data
US 2008/0190787 A1 Aug. 14, 2008

Related U.S. Application Data

(63) Continuation-in-part of application No. 11/377,766, filed on Mar. 15, 2006, now abandoned.

(51) Int. Cl.
A61C 15/00 (2006.01)
(52) U.S. Cl. .......................................... 132/325
(58) Field of Classification Search .................. 132/321, 132/323–328; 118/420, 123, 423; 206/63.3, 206/63.5; 401/121, 122
See application file for complete search history.

(56) References Cited

U.S. PATENT DOCUMENTS

| 1,455,673 | A | * | 5/1923 | Shalek | 242/138 |
| 2,128,701 | A | | 8/1938 | Gelinsky | |
| 3,094,996 | A | | 6/1963 | Lewis | |
| 3,830,247 | A | | 8/1974 | Kaphalakos | |
| 4,019,522 | A | | 4/1977 | Elbreder | |
| 5,065,861 | A | | 11/1991 | Greene et al. | |
| 5,607,050 | A | * | 3/1997 | Dolan et al. | 206/63.5 |
| 5,765,740 | A | | 6/1998 | Ferguson | |
| 5,911,829 | A | | 6/1999 | Maksudian et al. | |
| 6,676,320 | B1 | * | 1/2004 | Wainer | 401/122 |
| 6,705,328 | B1 | * | 3/2004 | Ramirez | 132/322 |
| 2008/0257377 | A1 | * | 10/2008 | Burrows | 132/322 |

OTHER PUBLICATIONS

U.S. Appl. No. 11/377,766; titled "Hygienic Dental Floss"; filed Mar. 15, 2006; inventor Ted K. Grosse; copy enclosed (7 pages).

* cited by examiner

Primary Examiner — Rachel R Steitz
(74) Attorney, Agent, or Firm — J. Bennett Mullinax, LLC

(57) ABSTRACT

A dental floss container is provided that may include a container that defines a fluid chamber. A hygienic fluid can be present and may be disposed in the fluid chamber of the container. A spool of dental floss is located in the fluid chamber and engages the hygienic fluid. The spool of dental floss may have a center axis that is oriented in the vertical direction.

18 Claims, 5 Drawing Sheets

HYGIENIC DENTAL FLOSS

CROSS REFERENCE TO RELATED APPLICATION

This application is a continuation-in-part and claims the benefit of U.S. application Ser. No. 11/377,766 filed on Mar. 15, 2006 and entitled, "Hygienic Dental Floss." U.S. application Ser. No. 11/377,766 is incorporated by reference herein in its entirety for all purposes. U.S. application Ser. No. 11/377,766 claims the benefit of U.S. Provisional Application Ser. No. 60/661,875 filed on Mar. 15, 2005. U.S. Provisional Application Ser. No. 60/661,875 is incorporated by reference herein in its entirety for all purposes.

FIELD OF THE INVENTION

The present invention relates generally to oral hygiene. More particularly, the present application involves a dental floss container that includes a hygienic fluid configured to be carried on the dental floss for subsequent application to the user during flossing.

BACKGROUND

Proper dental and periodontal hygiene typically includes regular flossing in addition to routine brushing. Furthermore, it is usually recommended or desired to periodically apply hygienic fluids to the teeth such as fluorides, mouthwash, antiseptics, whiteners and similar substances. However, because performing both tasks is time consuming, many people skip one or both.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which.

Figure 1:
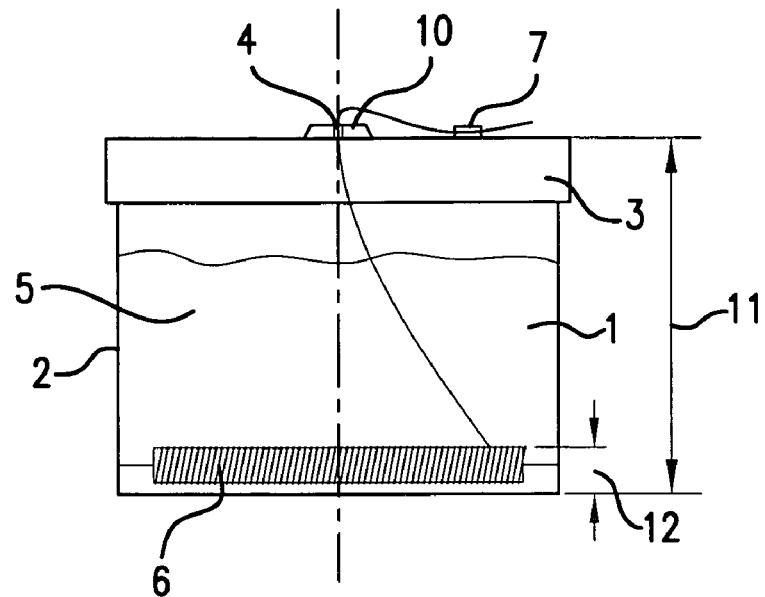
FIG. 1 is a side elevation view of a dental floss container in accordance with one exemplary embodiment.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a dental floss container 20 capable of holding dental floss 42 and a hygienic fluid 38. The dental floss 42 may be provided with the hygienic fluid 38 for subsequent application to the teeth and/or gums of the user.

In accordance with the exemplary embodiment illustrated in FIG. 1., the device includes a hollow container 1 having a lower surface with a plurality of sidewalls 2 extending upwardly therefrom, a top and an interior fluid chamber. A cap 3 is hermetically sealed to the top end of the container 1 and includes a small opening 4 thereon. Within the fluid chamber is a predetermined hygienic solution 5 such as tooth whitener, fluoride, mouthwash, plaque remover, peroxide or any other similar substance. Also received within the chamber and submerged in the solution is a horizontally disposed, low-profile spool 6 having dental floss spirally wrapped thereabout. The positioning and configuration of the spool assures that all of the floss wrapped thereabout is saturated with solution.

The dental floss exits the container 1 via the cap opening 4. A liquid impermeable seal 10 is formed about the floss to prevent the hygienic solution from seeping from the container. Immediately adjacent the cap opening 4 is a small blade 7 for severing the dental floss. The container may be constructed with a transparent or translucent material allowing a user to observe the hygienic solution and submerged floss. The tint and color of the translucent material can be varied.

When flossing, a user simply grasps and extends the dental floss until a desired length is available. The selected length of floss is severed and is used in a conventional fashion. Because the floss is saturated with the solution, the solution will be applied to the teeth as the user flosses.

The container 1 has a height 11 and the low-profile spool 6 has a height 12 as shown in FIG. 1. The height 12 of the low-profile spool 6 is such that it can be completely located in the lower portion of the chamber that contains the hygienic solution 5. In accordance with one exemplary embodiment, the height 12 is one third or less than the height 11 of the portion of the container 1 into which the hygienic solution 5 is located. However, other exemplary embodiments are possible in which the height 12 is from one fifth to one half of the height 11 of the portion of the container 1 into which the hygienic solution 5 is located. A low-profile arrangement allows for the maximum amount of hygienic solution 5 to be imparted onto the dental floss of the low-profile spool 6 for inclusion thereon and subsequent application.

The container 1 is arranged so that the cap 3 extends along the entire length of the low-profile spool 6. As shown in FIG. 1, the cap 3 is located above the low-profile spool 6 and extends across its entire length. The cap 3 is arranged so that it is located an equal distance from the low-profile spool 6 along the entire length of the low-profile spool 6. Such an arrangement allows for the maximum amount of hygienic solution 5 to be stored in the container 1 and evenly distributes the weight of the container 1 and hygienic solution 5 to provide stability to the overall arrangement. However, it is to be understood that other arrangements are possible in which the cap 3 is not located at the same distance from the low-profile spool 6 along the entire length of the low-profile spool 6.

Figure 2:
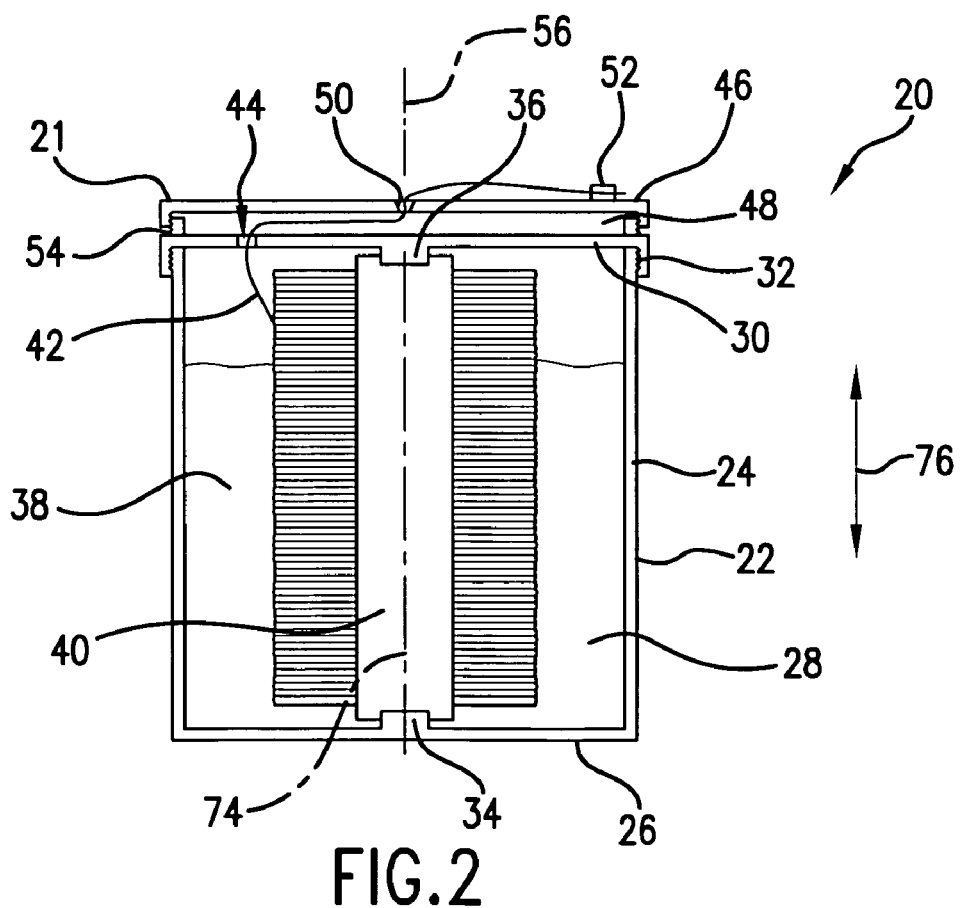
FIG. 2 is a side elevation view of a dental floss container in accordance with another exemplary embodiment.
Figure 3:
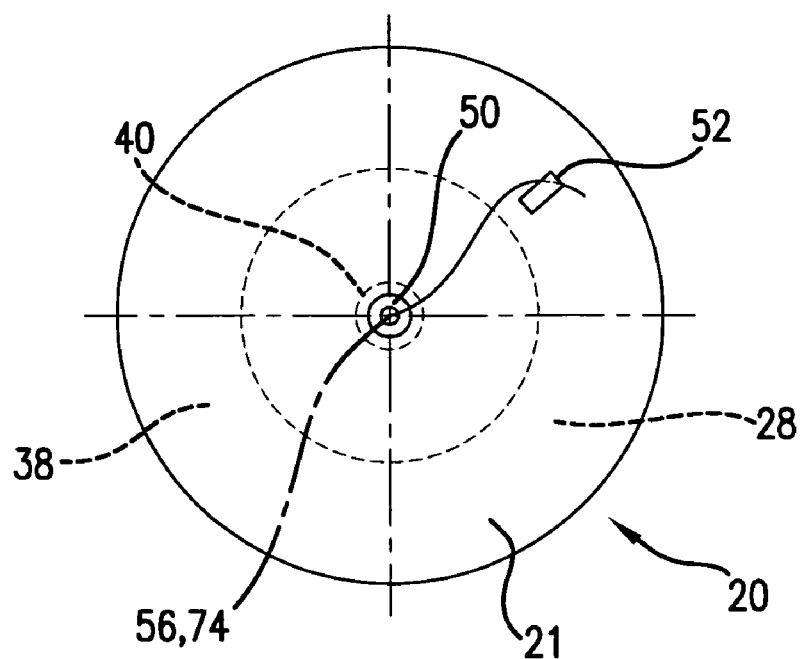
FIG. 3 is a top plan view of the dental floss container of FIG. 2.

An additional exemplary embodiment of the dental floss container 20 is shown in FIGS. 2 and 3. Here, the dental floss container 20 has a container 22 that has a round sidewall 24. However, it is to be understood that other exemplary embodiments are possible in which the sidewalls 24 of the container 22 are not round but are variously shaped. The container 22 has a bottom 26, from which the sidewall 24 extends, and that with the sidewall 24 forms a fluid chamber 28. Hygienic fluid 38 may be located in the fluid chamber 28. The hygienic fluid 38 can be a fluoride, mouthwash, antiseptic, whitener, plaque remover, or peroxide in accordance with certain exemplary embodiments. Further, it is to be understood that the hygienic fluid 38 can be other substances in accordance with other exemplary embodiments.

The dental floss container 20 includes a cap 21 that is located at the top end of the container 22. The cap 21 functions to close the upper end of the container 22 and prevent hygienic fluid 38 from inadvertently flowing from the fluid chamber 28. The dental floss 42 is arranged into a spool and is located in the fluid chamber 28 so that it engages the hygienic fluid 38. Again, this arrangement causes the hygienic fluid 38 to be carried on the dental floss 42 so that a user may obtain both the benefits of flossing with the dental floss 42 and the benefits associated with the particular hygienic fluid 38 associated therewith.

The cap 21 is illustrated as having both an inner cap 30 and an outer cap 46. However, it is to be understood that other exemplary embodiments are possible in which the cap 21 does not include the inner and outer caps 30 and 46. The inner cap 30 faces the interior of the container 22 and the outer cap 46 faces the exterior of the dental floss container 20 and forms an upper surface thereof. The inner cap 30 is provided with threads 32 that engage corresponding threads of the container 22 so that the inner cap 30 can be attached to and removed from the container 22 as desired. Removal of the inner cap 30 from the container 22 may cause a corresponding removal of the outer cap 46 and other portions of the cap 21 so that the fluid chamber 28 can be accessed by a user. The user may thus add replacement hygienic fluid 38 and dental floss 42 once they become depleted thus allowing the dental floss container to be a reusable item. However, it is to be understood that the hygienic fluid 38 and the dental floss 42 may be accessed and replaced through a different area in accordance with other embodiments. Further, other exemplary embodiments exist in which the cap 21 cannot be removed from the container 22 such that the hygienic fluid 38 and the dental floss 42 are not replaceable.

The spool of dental floss 42 can be oriented in the container 22 so that its center axis 74 extends in the vertical direction 76 of the dental floss container 20. Such an arrangement may allow for hygienic fluid 38 to be imparted onto the dental floss 42 even when the level of hygienic fluid 38 becomes depleted since the dental floss 42 can be spirally wrapped along the entire length of the spool of dental floss 42. The dental floss 42 can be wrapped around a core 40 which is in turn rotationally mounted onto a pair of mounting posts 34 and 36. Pulling of the dental floss 42 may thus cause the spool of dental floss 42 and core 40 to rotate about the mounting posts 34, 36 and with respect to other portions of the dental floss container 20. Vertical orientation of the center axis 74 of the spool of dental floss 42 may allow for the weight of the dental floss container 20 to be more evenly distributed and thus have more stability imparted thereto. The mounting post 34 can extend upwards from the bottom 26 of the container 22, and the mounting post 36 can extend downwards from the bottom of the inner cap 30 of the cap 21. The mounting posts 34 and 36 may be integrally formed with these components or may be separate pieces that are attached thereto.

The container 22 can have a center axis 56 that is oriented in the vertical direction 76 and passes through the center of the bottom 26 of the container 22. In accordance with certain exemplary embodiments, the sidewall 24 is round such that the container 22 is round. Here, the center axis 56 may pass through the center of the container 22. The spool of dental floss 42 can be oriented so that its center axis 74 is coaxial with the center axis 56 of the container 22. Other exemplary embodiments are possible, however, in which both the center axis 56 and the center axis 74 are vertically oriented yet are not coaxial with one another. Use of a round sidewall 24 and hence a round container 22 may assist in adding stability to the dental floss container 10.

The inner cap 30 defines an opening 44. Opening 44 may be located at any portion along the surface of inner cap 30. As shown in FIG. 2, opening 44 is located radially outward from the center axis 74 of the spool of dental floss 42. Other arrangements are possible in which the opening 44 is located at the center of the inner cap 30 such that the center axis 74 passes through the opening 44. The inner cap 30 and the outer cap 46 are arranged so that a space 48 is defined therebetween. In accordance with one exemplary embodiment, the outer cap 46 is provided with threads 54 that engage complimentary threads on the inner cap 30 so that the outer cap 46 can be removed from the inner cap 30 to access the space 48. However, other exemplary embodiments are possible in which the threads 54 are not present such that the space 48 cannot be accessed by the user.

A liquid impermeable seal 50 is located on the outer cap 46. The liquid impermeable seal 50 can be positioned at any location on the outer cap 46. As shown in FIGS. 2 and 3, the liquid impermeable seal 50 is located on the outer cap 46 such that the center axis 74 of the spool of dental floss 42 passes through the liquid impermeable seal 50. In this regard, the liquid impermeable seal 50 is located at the center of the outer cap 46. The liquid impermeable seal 50 is constructed so that dental floss 42 carrying the hygienic fluid 38 can pass across the liquid impermeable seal 50 yet still retain sufficient hygienic fluid 38 thereon for subsequent application to the user. Hygienic fluid 38 in the space 48 may be prevented from dripping out of the cap 21 through the presence of the liquid impermeable seal 50 should the dental floss container 20 be overturned. Location of the liquid impermeable seal 50 along the center axes 56 and 74 may allow for ease of alignment and may assist in maintaining the liquid impermeable seal 50 in a normally closed position. A blade 52 is located on the outer surface of the cap 21 to assist in cutting of the dental floss 42 to a desired length.

Various portions of the dental floss container 20, such as the cap 21 and/or container 22, can be transparent or translucent. The various portions of the dental floss container 20 may additionally be tinted. Observation of the amount of hygienic fluid 38 and the dental floss 42 allows for their replacement at a convenient time. Further, tinting of the various portions of the dental floss container 20 may act to inform the user of the particular hygienic fluid 38 housed within the container 22. For example, a red tinted container 22 may signify that a tooth whitener is present within container 22, while a blue tinted container 22 may indicate that mouthwash is the hygienic fluid 38 housed within the container 22.

Figure 4:
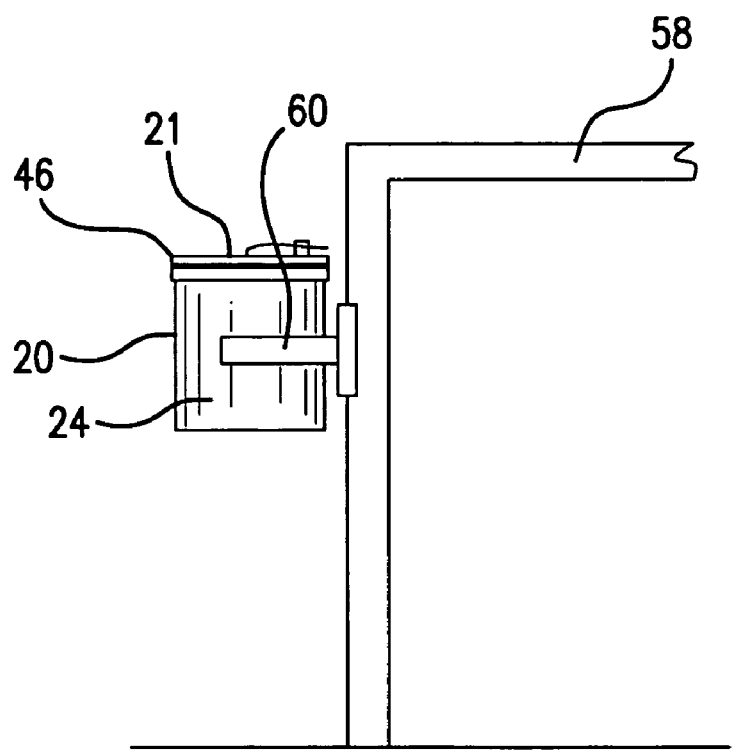
FIG. 4 is a side elevation view of a dental floss container attached to a table in accordance with another exemplary embodiment.

FIG. 4 illustrates an alternative exemplary embodiment of the dental floss container 20. As shown, a clip 60 is present and is attached to a table 58 or other structure. The clip 60 can be made so as to frictionally engage the sidewall 24 of the container 22 for use in retaining the container 22 thereon. In this manner, the dental floss container 20 may be retained to the table 58. A healthcare provide, such as an oral hygienist, may locate the dental floss container 20 at a desirable location at their place of work in order to conveniently dispense dental floss 42 therefrom. The clip 60 may be arranged so as to retain the container 22 thereon in a variety of fashions. For example, the clip 60 may include a base onto which the container 22 rests, may employ mechanical fasteners, or may use adhesives in order to retain the container 22 thereon.

Figure 5:
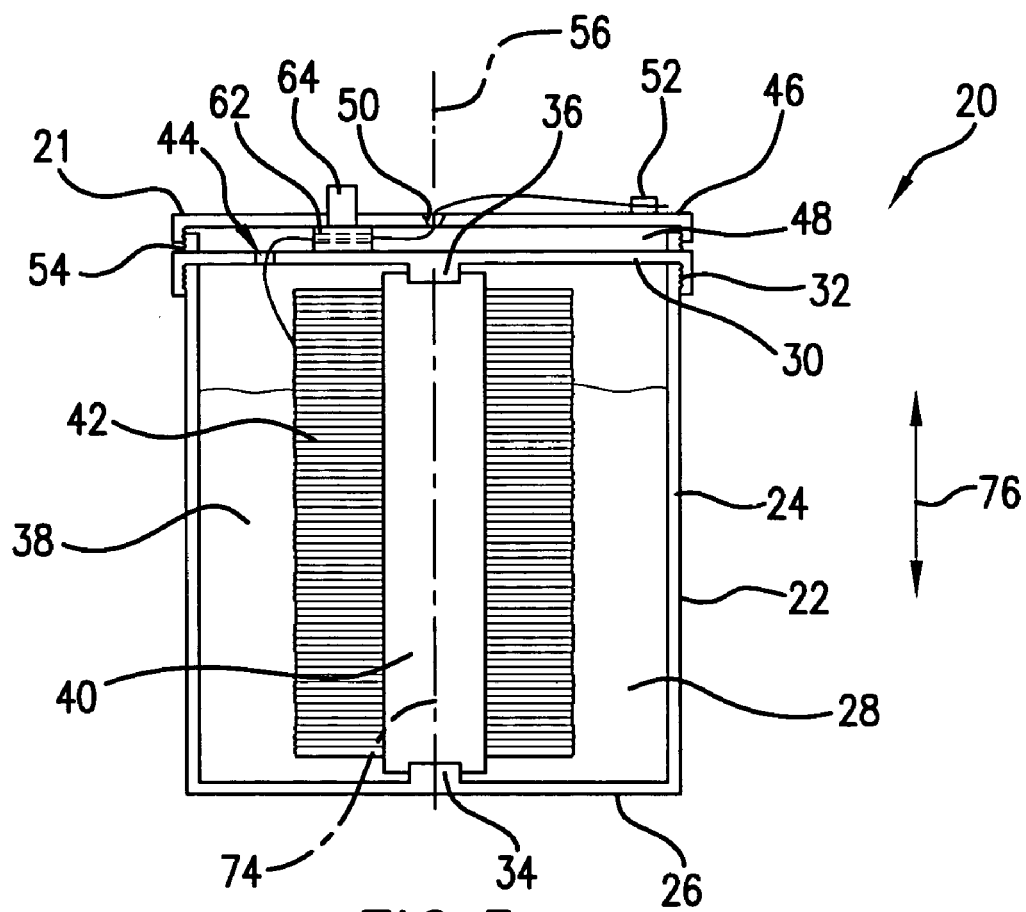
FIG. 5 is a side elevation view of a dental floss container in accordance with another exemplary embodiment.

During use of dental floss 42, a user will typically dispense a length of dental floss 42 sufficient to wrap one around a finger on one hand, and the opposite end around a finger on the other hand. The middle portion of the dental floss 42 is thus used to clean the teeth of the user while the end portions are typically discarded without being used specifically to contact the teeth or gums. FIG. 5 illustrates one exemplary embodiment of the dental floss container 20. The dental floss container 20 is similar to the exemplary embodiment discusses with respect to FIGS. 2 and 3. However, the exemplary embodiment in FIG. 5 includes a wiper 62 and button 64. Wiper 62 is located in the space 48, and button 64 extends through the outer cap 46 to an outer surface of the outer cap 46. The wiper 62 is configured for engaging the dental floss 42 so that hygienic fluid 38 carried on the dental floss 42 is wiped therefrom, or is at least substantially wiped therefrom.

The button 64 may be manually pressed by a user in order to impart a force onto the wiper 62. This force may cause the wiper 62 to engage the dental floss 42 and thus wipe hygienic fluid 38 from the dental floss 42 as desired. The button 64 may be released by the user so that the wiper 62 no longer engages the dental floss 42 and thus no longer removes hygienic fluid 38 therefrom. In this manner, a user may press button 64 to cause wiper 62 to engage the dental floss 42. Next, the user can pull the dental floss 42 a desired length and then release the button 64. Release of button 64 causes the wiper 62 to disengage the dental floss 42 such that hygienic fluid 38 is now retained on the dental floss 42. The user can continue to pull the dental floss 42 a desired length and then again press the button 64. The wiper 62 once again engages so that hygienic fluid 38 is removed from the dental floss 42. The user can then cut the dental floss 42 from the dental floss container 20 with the use of blade 52. The resulting dental floss 42 piece will have no hygienic fluid 38 on its ends, but will have hygienic fluid 38 present between the two ends. The user can twirl the ends of the hygienic fluid 38 about his or her fingers without transferring hygienic fluid 38 onto his or her fingers. The dental floss 42 can be used in the previously described manner as the benefits of the hygienic fluid 38 in the middle section of the dental floss 42 will be realized.

As such, the exemplary embodiment in FIG. 5 allows the user to wipe hygienic fluid 38 from the dental floss 42 as desired. The wiper 62 can be arranged as that shown in FIG. 6. Here, the dental floss 42 is disposed through an aperture that is made completely through the wiper 62. The wiper 62 may be made out of a flexible, resilient material such as rubber. Hygienic fluid 38 on the dental floss 42 will remain thereon as the dental floss 42 passes through the wiper 62. As such, the wiper 62 is in a non-wiping orientation in FIG. 6.

Figure 6:
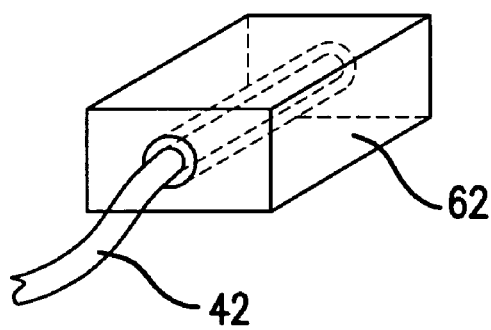
FIG. 6 is a perspective view of a wiper that is not engaging and wiping dental floss in accordance with one exemplary embodiment.
Figure 7:
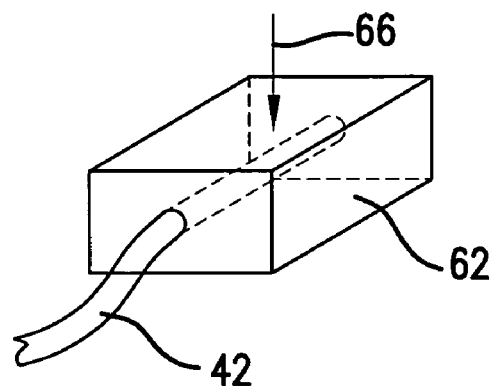
FIG. 7 is a perspective view of the wiper of FIG. 6 during engagement and wiping of the dental floss.

Application of force 66, for example as through the pressing of a button 64 in FIG. 5, onto the wiper 62 is shown in FIG. 7. Force 66 causes the wiper 62 to compress such that the aperture though the wiper 62 is closed thus causing the wiper 62 to snuggly contact the dental floss 42. The wiper 62 and force 66 can be sized and selected such that the wiper 62 can engage and wipe the dental floss 42 yet still allow the dental floss 42 to be pulled through the wiper 62. As the wiper 62 engages the dental floss 42, hygienic fluid 38 thereon is wiped and removed therefrom. Removal of force 66 causes the wiper 62 to resume its original orientation as shown in FIG. 6 through inherent resiliency of the material making up the wiper 62.

Although described as removing the hygienic fluid 38 from the dental floss 42, it is to be understood that the dental floss container 20 can be arranged so that the hygienic fluid 38 is completely removed, substantially removed, or at least partially removed therefrom. As such, the resulting length of dental floss 42 can have varying amounts of hygienic fluid 38 disposed along its length. Wiping of the hygienic fluid 38 from undesired sections of the dental floss 42 prevents waste of the hygienic fluid 38 as it is still contained in the dental floss container 20 for future use.

Figure 8:
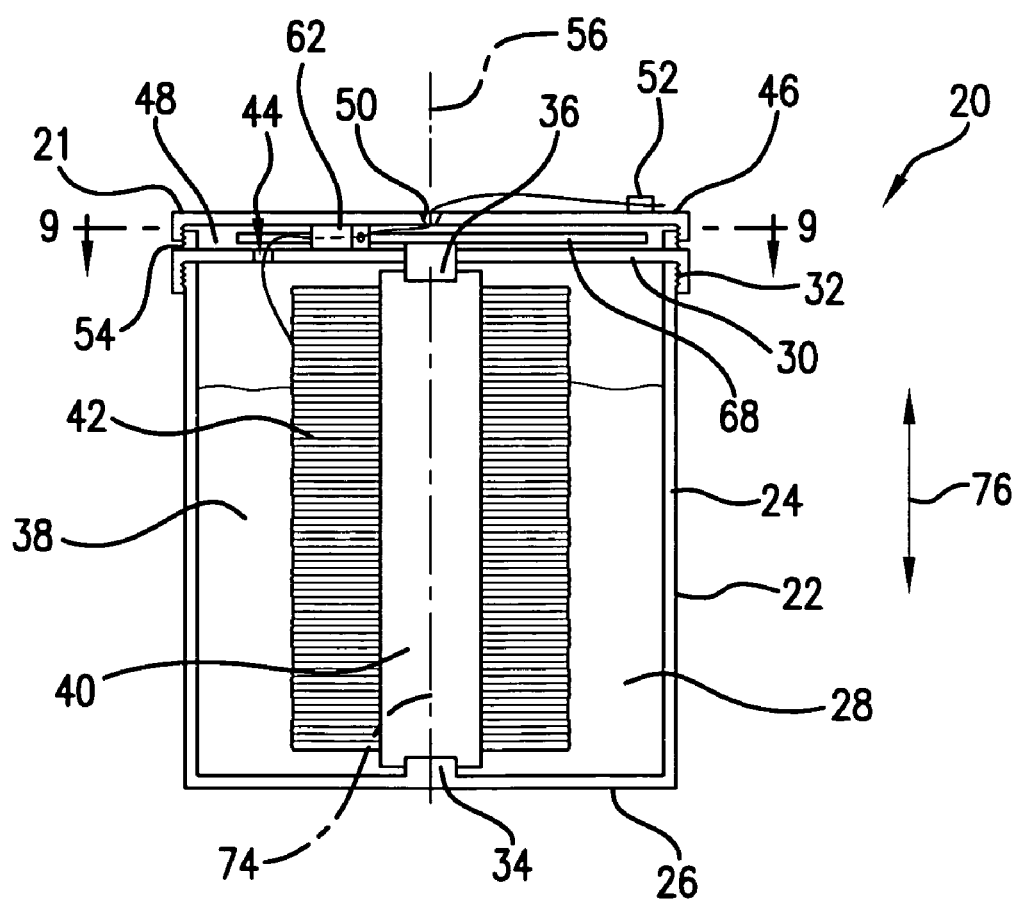
FIG. 8 is a side elevation view of a dental floss container in accordance with another exemplary embodiment.
Figure 9:
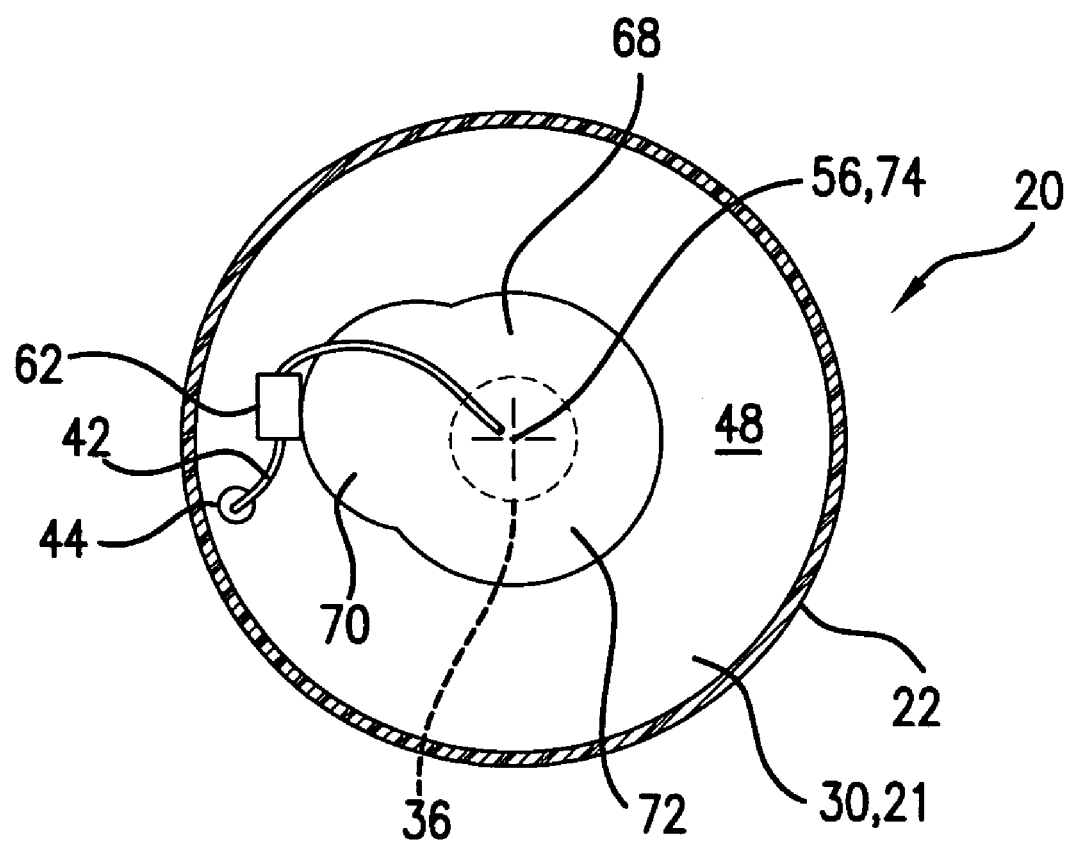
FIG. 9 is a cross-sectional view taken along line 9-9 of FIG. 8.

FIGS. 8 and 9 illustrate an exemplary embodiment of the dental floss container 20 in which an automatic wiping of the dental floss 42 occurs. In this regard, a cam 68 is present in the space 48. Cam 68 is rigidly attached to the mounting post 36. In this regard, rotation of the spool of dental floss 42 may be translated into rotational motion of the cam 68. In accordance with other arrangements, mounting post 36 may be stationary with respect to the cam 68. Here, rotational motion of the spool of dental floss 42 is translated to the cam 68 without going through the mounting post 36. As illustrated more clearly with reference to FIG. 9, the cam 68 includes a compressing portion 70 and a non-compressing portion 72. Initially, the cam 68 can be oriented so that the compressing portion 70 engages the wiper 62 and causes a force to be imparted thereon in order to cause wiping of the dental floss 42.

The user may pull the dental floss 42 in order to dispense a length for use in conducing oral hygiene. Pulling of the dental floss 42 may cause a subsequent rotation of the spool of dental floss 42 and hence a corresponding rotation of the cam 68. The compressing portion 70 engages the wiper 62 so that hygienic fluid 38 is wiped from the dental floss 42. Continued pulling of the dental floss 42 causes rotation of the cam 68 so that the non-compressing portion 72 is proximate to the wiper 62 so that hygienic fluid 38 is maintained on the dental floss 42. Additional pulling of the dental floss 42 once again causes rotation of the cam 68 so that the compressing portion 70 functions to apply force to the wiper 62 to wipe the dental floss 42. The user may then cut the dental floss 42 with the blade 52. The resulting dental floss 42 includes ends that are wiped and a middle portion that includes the hygienic fluid 38.

Various alternate arrangements of the dental floss container 10 are possible in which the cam 68 is variously arranged to effect an automatic wiping of the dental floss 42. Further, the dental floss container 20 can be made so that various ways of translating motion and applying forces to the wiper 62 are possible. As such, the exemplary embodiment shown is for purposes of illustration and it is to be understood that other methods are possible. Any number of sections that have hygienic fluid 38 and that do not have hygienic fluid 38 can be realized. For example, the dental floss container 20 can be constructed so that it automatically wipes the dental floss 42 so that up to ten sections have hygienic fluid 38 and so that up to ten sections do not have hygienic fluid 38 located thereon.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A hygienic dental floss container, comprising:
   a hollow container having a top and an interior fluid chamber;
   a cap hermetically sealed to the top of the container, the cap having a small opening thereon, wherein the cap has an inner cap that directly faces and at least partially defines the interior fluid chamber and is releasably attachable to the container by a threaded engagement, wherein the cap has an outer cap that is releasably attachable to the inner cap by a second threaded engagement and that has a lower surface that directly faces an upper surface of the inner cap such that an empty space is between the lower surface and the upper surface, and wherein the small opening extends through the outer cap;
   a predetermined oral hygienic solution received within the interior fluid chamber; and
   a horizontally-disposed, low-profile spool submerged in the solution and positioned within a lower portion of the interior fluid chamber, the spool having dental floss spirally wrapped thereabout, a portion of the dental floss extending from the small opening of the cap allowing a user to apply the hygienic solution to one's teeth while flossing, wherein the cap is located above the spool and along the entire length of the spool, and wherein the cap is located the same distance from the spool along the entire length of the spool, wherein the small opening of the cap is located at a center position of the cap;
   wherein the spool has a height that is from one fifth to one half of a height of the interior fluid chamber, and wherein the oral hygienic solution and the spool are replaced after their depletion so that the hygienic dental floss container is reusable.

2. The hygienic dental floss container as set forth in claim 1, further comprising a small blade immediately adjacent the cap opening for severing the dental floss.

3. The hygienic dental floss container as set forth in claim 2, wherein the container is constructed with either of a transparent or translucent material allowing a user to observe the hygienic solution and submerged dental floss.

4. The hygienic dental floss container as set forth in claim 3, further comprising a liquid impermeable seal between the cap opening and the dental floss to prevent the solution from seeping from the container.

5. The hygienic dental floss container as set forth in claim 4, wherein the container is tinted when the container is constructed with the translucent material.

6. The hygienic dental floss container as set forth in claim 1, wherein the height of the interior fluid chamber is at least three times the height of the spool.

7. A dental floss container, comprising:
   a container defining a fluid chamber;
   a hygienic fluid disposed in the fluid chamber of the container; and
   a spool of dental floss located in the fluid chamber and engaging the hygienic fluid, wherein the spool of dental floss has a center axis that is oriented in a vertical direction,
   wherein the container has a center axis that is coaxial with the center axis of the spool of dental floss, and wherein the spool of dental floss is capable of being rotated about the center axis of the container and the center axis of the spool of dental floss;
   a cap located on an upper end of the container wherein the cap has an opening to allow dental floss to be passed therethrough, wherein the opening is not located along the center axis of the spool of dental floss; and
   a wiper located radially between the opening of the cap and the center axis of the spool of dental floss, wherein the wiper is spaced in a radial direction from the center axis such that a space that extends in the radial direction is present between the wiper and the center axis, and wherein the wiper is spaced in the radial direction from the opening of the cap such that a second space is present that extends in the radial direction between the opening and the wiper, wherein the wiper is configured to remove at least some of the hygienic fluid from the dental floss upon being moved across the wiper.

8. The dental floss container as set forth in claim 7, wherein the cap has a liquid impermeable seal configured for preventing at least some of the hygienic fluid from exiting out of the cap, wherein the dental floss is configured for passing across the liquid impermeable seal during dispensing of the dental floss.

9. The dental floss container as set forth in claim 8, wherein the liquid impermeable seal is located along the center axis of the container, and wherein the liquid impermeable seal is located along the center axis of the spool of dental floss.

10. The dental floss container as set forth in claim 8, wherein the cap is releasably attachable to the container, wherein the cap has an inner cap and an outer cap, wherein a space is defined between the inner cap and the outer cap.

11. The dental floss container as set forth in claim 10, wherein the opening of the cap is through the inner cap to allow the dental floss to be passed therethough and into the space between the inner cap and the outer cap.

12. The dental floss container as set forth in claim 8, further comprising:
   a blade located on the outer surface of the cap and configured for cutting the dental floss; and
   a pair of mounting posts, wherein the spool of dental floss is mounted onto the pair of mounting posts, wherein one of the mounting posts is located at a bottom of the container, and wherein the other one of the mounting posts is located at the cap.

13. The dental floss container as set forth in claim 7, wherein the hygienic fluid is selected from a group consisting of tooth whitener, fluoride, mouthwash, plaque remover and peroxide.

14. The dental floss container as set forth in claim 7, further comprising a clip configured for attachment to a table, wherein the container has a sidewall that is round in shape, and wherein the round sidewall of the container is capable of being attached to the clip so as to effect retention of the container to the table.

15. A dental floss container, comprising:
   a container defining a fluid chamber, wherein the container has a center axis, wherein the container has a bottom wall, a side wall, and an upper wall that at least partially define the fluid chamber, wherein the upper wall has an opening;

a hygienic fluid disposed in the fluid chamber of the container;

a spool of dental floss located in the fluid chamber and engaging the hygienic fluid, wherein the dental floss is passed through the opening; and a wiper configured for at least partially removing the hygienic fluid from the dental floss such that the dental floss is capable of being dispensed with unequal amounts of the hygienic fluid disposed along the length thereof, wherein a portion of the wiper that engages the dental floss also engages the upper wall and is located outside of the fluid chamber such that the upper wall is located directly between the portion of the wiper that engages the dental floss and the fluid chamber, wherein the wiper is located radially between the opening and the center axis, wherein the wiper is spaced in a radial direction from the center axis such that a space that extends in the radial direction is present between the wiper and the center axis, and wherein the wiper is spaced in the radial direction from the opening such that a second space is present that extends in the radial direction between the opening and the wiper.

16. The dental floss container as set forth in claim 15, further comprising a button configured for being manually actuated by a user in order to actuate the wiper to change between orientations effecting wiping of hygienic fluid from the wiper blade and not effecting wiping of hygienic fluid from the wiper blade.

17. The dental floss as set forth in claim 15, further comprising a cam configured for automatically actuating the wiper to change between orientations effecting wiping of hygienic fluid from the wiper blade and not effecting wiping of hygienic fluid from the wiper blade.

18. The dental floss as set forth in claim 17, wherein the spool of dental floss is configured for being rotated with respect to the container, wherein the cam is in communication with the spool of dental floss such that rotation of the spool of dental floss effects rotation of the cam.

* * * * *

UNITED STATES PATENT AND TRADEMARK OFFICE
CERTIFICATE OF CORRECTION

| | | |
|---|---|---|
| PATENT NO. | : 7,987,861 B2 | Page 1 of 1 |
| APPLICATION NO. | : 12/009507 | |
| DATED | : August 2, 2011 | |
| INVENTOR(S) | : Ted K Grosse | |

It is certified that error appears in the above-identified patent and that said Letters Patent is hereby corrected as shown below:

In Claim 7 at col. 7 line 67, the word "and" should be deleted.

In Claim 7 at col. 8 line 10, a --,-- should be inserted after the word container Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

PATENT NO.         : 7,987,861 B2                                                    Page 1 of 1
APPLICATION NO.    : 12/009507
DATED              : August 2, 2011
INVENTOR(S)        : Ted K Grosse It is certified that error appears in the above-identified patent and that said Letters Patent is hereby corrected as shown below:

In col. 5 line 10, the word "provide" should be replaced with the word --provider--.
In col. 5 line 54, the phrase "hygienic fluid 38" should be replaced with the phrase --dental floss 42--.
In Claim 11 at col. 8 line 41, the word "therethough" should be replaced with the word --therethrough--.

Signed and Sealed this
Second Day of October, 2012

David J. Kappos
*Director of the United States Patent and Trademark Office*